United States Patent
Park et al.

(10) Patent No.: US 10,828,224 B2
(45) Date of Patent: Nov. 10, 2020

(54) POWER TRANSMITTING DEVICE AND MOTION ASSISTANCE APPARATUS INCLUDING THE SAME

(71) Applicant: Samsung Electronics Co., Ltd., Suwon-si (KR)

(72) Inventors: Youngjin Park, Seoul (KR); Taesin Ha, Seongnam-si (KR); Jeonghun Kim, Hwaseong-si (KR); Se-Gon Roh, Suwon-si (KR); Youn-Baek Lee, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 975 days.

(21) Appl. No.: 15/334,500

(22) Filed: Oct. 26, 2016

(65) Prior Publication Data

US 2017/0128312 A1 May 11, 2017

(30) Foreign Application Priority Data

Nov. 5, 2015 (KR) .................. 10-2015-0155151

(51) Int. Cl.
*A61H 3/00* (2006.01)
*A61H 1/02* (2006.01)
(Continued)

(52) U.S. Cl.
CPC .............. *A61H 3/00* (2013.01); *A61F 2/68* (2013.01); *A61F 2/70* (2013.01); *A61H 1/0244* (2013.01);
(Continued)

(58) Field of Classification Search
CPC ..... A61F 2/68; A61F 2002/6854; A61H 3/00; A61H 2003/007; A61H 2201/1215;
(Continued)

(56) References Cited

U.S. PATENT DOCUMENTS

| 5,020,790 A * | 6/1991 | Beard .................. A61F 5/0102 482/4 |
| 2003/0062241 A1 | 4/2003 | Irby et al. |
| 2006/0260620 A1 | 11/2006 | Kazerooni et al. |
| 2010/0298746 A1 | 11/2010 | Shimizu et al. |
| 2013/0102398 A1 | 4/2013 | Kim et al. |

FOREIGN PATENT DOCUMENTS

| CN | 103260576 A | 8/2013 |
| FR | 2.208.478 A5 | 6/1974 |

(Continued)

OTHER PUBLICATIONS

Extended European Search Report issued by the European Patent Office dated Mar. 31, 2017 for corresponding EP Patent Application No. 16197231.0.
First Office Action issued by the CNIPA dated Dec. 18, 2019 for Chinese Patent Application No. 201610423477.X.
1st Office Action issued by the Japanese Patent Office dated Jul. 14, 2020 for the corresponding Japanese Patent Application No. 2016-180645.

*Primary Examiner* — Christopher D. Prone
(74) *Attorney, Agent, or Firm* — Harness, Dickey and Pierce, P.L.C.

(57) ABSTRACT

A motion assistance apparatus may include a power transmitting device having an input link provided to rotate with respect to a base, an output link provided to rotate with respect to the base, a first shaft connected to the input link in a direction intersecting an axial direction of the input link, a first connecting link connected to the first shaft, a second shaft connected to the first connecting link in a direction intersecting an axial direction of the first shaft, a second connecting link connected to the second shaft, and a third shaft connected between the second connecting link and the output link in a direction intersecting an axial direction of the second shaft.

32 Claims, 18 Drawing Sheets

(51) Int. Cl.
  *F16D 3/16* (2006.01)
  *A61F 2/70* (2006.01)
  *A61F 2/68* (2006.01)
  *F16H 21/06* (2006.01)
  *F16H 21/44* (2006.01)

(52) U.S. Cl.
  CPC ............... *F16D 3/16* (2013.01); *F16H 21/06* (2013.01); *F16H 21/44* (2013.01); *A61F 2002/701* (2013.01); *A61H 2201/1207* (2013.01); *A61H 2201/1215* (2013.01); *A61H 2201/1261* (2013.01); *A61H 2201/14* (2013.01); *A61H 2201/1436* (2013.01); *A61H 2201/163* (2013.01); *A61H 2201/165* (2013.01); *A61H 2201/1642* (2013.01); *A61H 2201/5058* (2013.01); *A61H 2201/5061* (2013.01); *A61H 2201/5071* (2013.01); *A61H 2201/5084* (2013.01); *A61H 2205/10* (2013.01)

(58) Field of Classification Search
  CPC ........ A61H 2201/14; A61H 2201/1436; A61H 2201/1445
  See application file for complete search history.

(56) References Cited

FOREIGN PATENT DOCUMENTS

| | | |
|---|---|---|
| JP | 59-026365 U | 2/1984 |
| JP | 10015861 A | 1/1988 |
| JP | 09038877 A | 2/1997 |
| JP | 2012165966 A | 9/2012 |
| JP | 2014050926 A | 3/2014 |
| KR | 20090125365 A | 12/2009 |
| KR | 20140021887 A | 2/2014 |
| WO | WO-2012/007014 A1 | 1/2012 |

\* cited by examiner

POWER TRANSMITTING DEVICE AND MOTION ASSISTANCE APPARATUS INCLUDING THE SAME

CROSS-REFERENCE TO RELATED APPLICATION

This application claims the priority benefit of Korean Patent Application No. 10-2015-0155151, filed on Nov. 5, 2015, in the Korean Intellectual Property Office, the disclosure of which is incorporated herein by reference in its entirety.

BACKGROUND

1. Field

Example embodiments relate to a power transmitting device and/or a motion assistance apparatus including the same.

2. Description of the Related Art

With the onset of rapidly aging societies, an increasing number of people may experience inconvenience and/or pain from joint problems. Thus, there may be a growing interest in motion assistance apparatuses enabling the elderly and/or patients having joint problems to walk with less effort. Furthermore, motion assistance apparatuses increasing muscular strength of human bodies may be developed for military purposes.

SUMMARY

Some example embodiments relate to a power transmitting device.

In some example embodiments, the power transmitting device may include an input link configured to rotate with respect to a base; an output link configured to rotate with respect to the base; a first shaft connected to the input link in a direction intersecting an axial direction of the input link; a first connecting link connected to the first shaft; a second shaft connected to the first connecting link in a direction intersecting an axial direction of the first shaft; a second connecting link connected to the second shaft; and a third shaft connected between the second connecting link and the output link in a direction intersecting an axial direction of the second shaft.

In some example embodiments, the output link and the input link are configured to rotate in a same direction.

In some example embodiments, the second shaft is configured to one of transfer power and block power between into the input link and the output link based on whether the axial direction of the input link matches the axial direction of the second shaft.

In some example embodiments, the axial direction of the first shaft is orthogonal to the axial direction of the input link, the axial direction of the second shaft is orthogonal to the axial direction of the first shaft, an axial direction of the third shaft is orthogonal to the axial direction of the second shaft, and an axial direction of the output link is orthogonal to the axial direction of the third shaft.

In some example embodiments, an axial direction of the third shaft is orthogonal to the axial direction of the input link.

In some example embodiments, an axial direction of the output link is orthogonal to the axial direction of the first shaft.

In some example embodiments, the power transmitting device may further include a locking device configured to maintain a relative angle formed by the second shaft with respect to a shaft of the input link.

In some example embodiments, the locking device includes a stopper configured to move relative to the output link to restrict a movement of the second connecting link.

In some example embodiments, the locking device further includes a first elastic member configured to provide an elastic force to the stopper in a direction that restricts the movement of the second connecting link.

In some example embodiments, the power transmitting device further includes a second elastic member configured to provide an elastic force to the second connecting link to urge the second connecting link to separate from the stopper.

In some example embodiments, the stopper includes a stopper body associated with the first elastic member, the stopper body configured to slide with respect to the output link; and a grip associated with the stopper body, the grip configured to provide friction to a user when the user grips the grip.

In some example embodiments, the locking device includes a magnetic body configured to magnetically couple the output link to least one of the first connecting link and the second connecting link.

In some example embodiments, the power transmitting device further includes a sensor configured to sense information related to a load applied to at least one of the input link, the output link, the first shaft, the first connecting link, the second shaft, the second connecting link, and the third shaft; and a controller configured to control the locking device based on the information sensed by the sensor.

In some example embodiments, the controller is configured to release the locking device when a value of the information sensed by the sensor exceeds a threshold.

In some example embodiments, the locking device includes a stopper configured to restrict a movement of the second connecting link; a first elastic member configured to provide an elastic force to the stopper in a first direction such that the stopper restricts the movement of the second connecting link; and a solenoid configured to provide an electromagnetic force to the stopper to move the stopper in a second direction opposite to the first direction when a current is applied such that the movement of the second connecting link is unrestricted by the stopper.

In some example embodiments, a second elastic member configured to provide an elastic force to the second shaft such that the relative angle between the second shaft and the shaft of the input link changes when the locking device is released.

In some example embodiments, the second elastic member is configured to provide the elastic force to the second connecting link such that power transfer between the input link and the output link is blocked.

In some example embodiments, the second elastic member is configured to provide the elastic force to the second shaft such that the second shaft rotates in a same direction as the axial direction of the input link.

In some example embodiments, the locking device includes a control motor configured to adjust a rotation angle of the third shaft.

Some example embodiments relate to a power transmitting device.

In some example embodiments, the power transmitting device includes an input link configured to receive power; an output link configured to output the power; and a plurality of connecting links connected between the input link and the output link, the plurality of connecting links configured to transmit or block the power transmission to the output link based on a rotation angle of at least one of the plurality of connecting links.

In some example embodiments, a shaft of the input link matches a shaft of the output link.

In some example embodiments, the plurality of connecting links includes a first connecting link configured to rotate relative to the input link; and a second connecting link configured to rotate relative to the first connecting link.

In some example embodiments, the plurality of connecting links transmit or block transmission of the power to the output link based on a rotation angle of the second connecting link.

In some example embodiments, the plurality of connecting links transmit the power to the output link when one of the plurality of connecting links is at a singular point.

Some example embodiments relate to a motion assistance apparatus.

In some example embodiments, the motion assistance apparatus includes a fixing device configured to attach to a first portion of a user; a support configured to support a second portion of the user; a driver configured to generate power; and a power transmitting device configured selectively transmit the power between the driver and the support, the power transmitting device including, an input link configured to receive the power from the driver; an output link connected to the support; and a plurality of connecting links connected between the input link and the output link, the plurality of connecting links configured to transmit or block transmission of the power to the output link based on a rotation angle of at least one of the plurality of connecting links.

Some example embodiments relate to power transmitting device.

In some example embodiments, the power transmitting device includes a plurality of rotatable links connected between a drive shaft of a motor and an output link, the plurality of rotatable links configured to selectively transmit a driving torque from the motor to the output link based on a relative angle between the drive shaft and at least one of the plurality of rotatable links.

In some example embodiments, the plurality of rotatable links includes at least a first rotatable link and a second rotatable link, the first rotatable link configured to pivot about the drive shaft via a first shaft to change the relative angle between the drive shaft and the second rotatable link.

In some example embodiments, an axial direction of the first shaft is orthogonal to an axial direction of the drive shaft.

In some example embodiments, the second rotatable link has a second shaft penetrating therethrough and attached to the first rotatable link.

In some example embodiments, the first rotatable link is configured to pivot between a first position in which the first rotatable link transmits a driving torque generated by the drive shaft to the second rotatable link and a second position in which the first rotatable link does not transmit the driving torque to the second rotatable link.

In some example embodiments, in the second position, the first rotatable link is configured spin about the second shaft such that the driving torque is not transmitted to the second rotatable link.

In some example embodiments, in the second position, the drive shaft and the second shaft are aligned.

In some example embodiments, in the second position, the drive shaft and the second shaft are aligned such that the axial direction of the drive shaft is same as the axial direction of the second shaft.

In some example embodiments, in the second position, the first rotating link and the second rotating link remain connected.

In some example embodiments, the power transmitting device further includes a releasable lock configured to selectively lock the first rotatable link at a first one of the first position and the second position.

In some example embodiments, the power transmitting device further includes a spring configured to rotate the first rotatable link to a second one of the first position and the second position, if the releasable lock is unlocked.

In some example embodiments, the power transmitting device further includes a sensor configured to sense a force applied by the drive shaft to one or more of the plurality of rotatable links; and a controller configured generate an instruction to unlock the releasable lock, if the force exceeds a threshold.

In some example embodiments, the power transmitting device further includes a solenoid configured to unlock the lock in response to the instruction from the controller.

Some example embodiments relate to a motion assistance apparatus.

In some example embodiments, the motion assistance apparatus includes a belt configured to attach to a waist of a user; a driver attached to the belt, the driver including the motor configured to generate the power; a support configured to be fixed to a limb of the user to assist a movement of the limb; and a power transmitting device configured to selectively transmit the power from the driver to the support via the output link.

In some example embodiments, the motion assistance apparatus further includes a sensor configured to sense information associated with a movement of the user; and a controller configured, determine whether the user is experiencing difficulty moving based on the information, and transmit an instruction to the power transmitting device to transmit the driving torque, if the user is experiencing difficulty moving.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
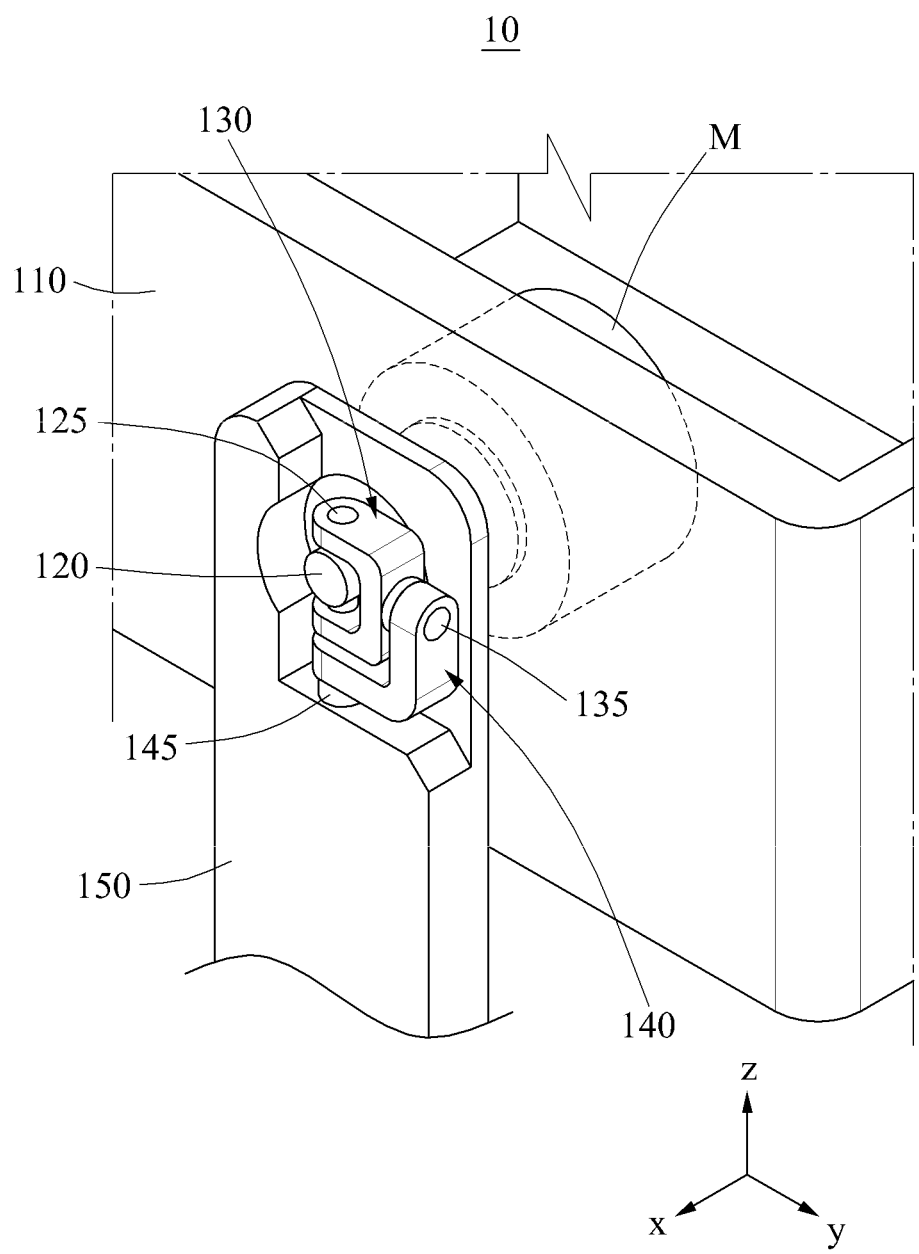
FIG. 1 is a perspective view illustrating a power transmitting device being in a power transmitting state according to example embodiments.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. Terms, such as those defined in commonly used dictionaries, should be interpreted as having a meaning that is consistent with their meaning in the context of the relevant art and/or this disclosure, and should not be interpreted in an idealized or overly formal sense unless expressly so defined herein.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

Various example embodiments will now be described more fully with reference to the accompanying drawings in which some example embodiments are shown. In the drawings, the thicknesses of layers and regions are exaggerated for clarity.

Figure 2:
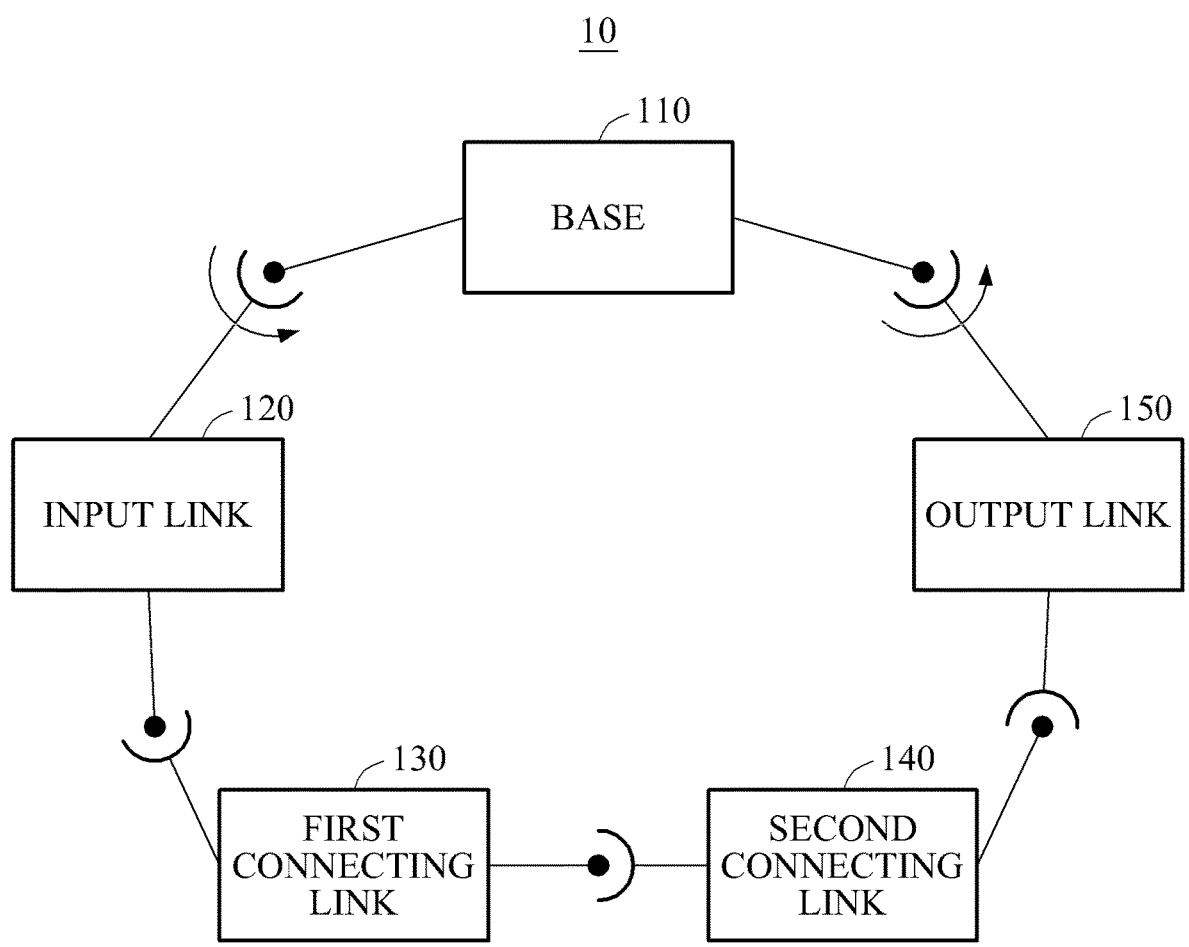
FIG. 2 is a diagram illustrating a power transmitting device being in a power transmitting state according to example embodiments.
Figure 3:
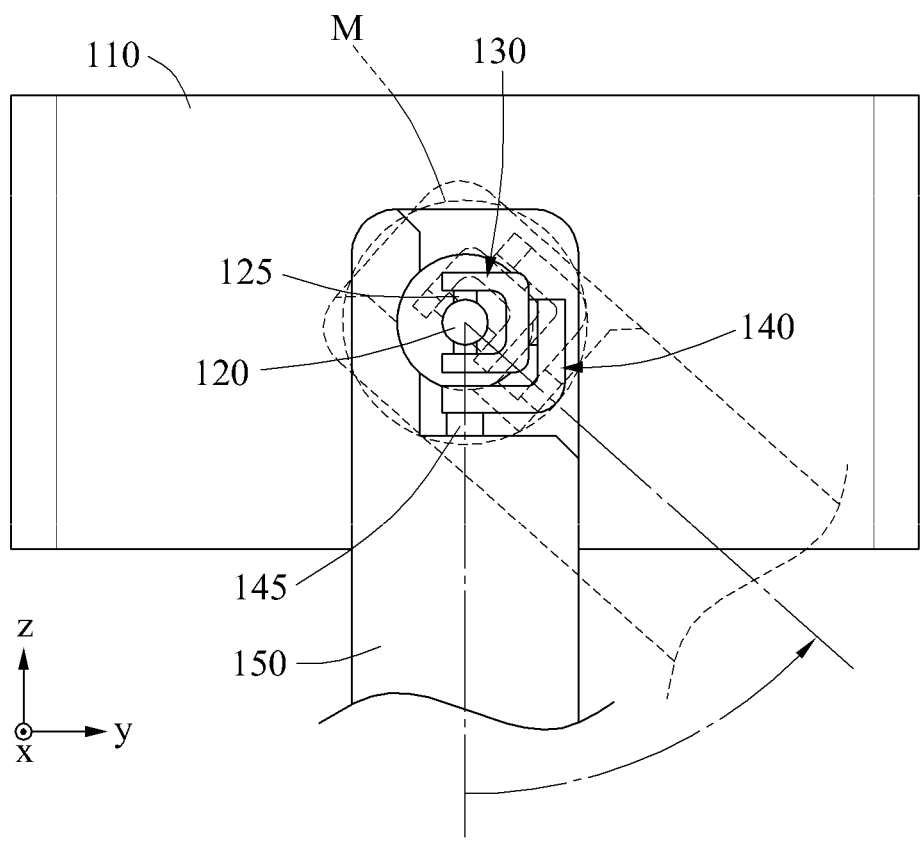
FIG. 3 is a view illustrating an operation of a power transmitting device being in a power transmitting state according to example embodiments.

FIG. 1 is a perspective view illustrating a power transmitting device being in a power transmitting state according to example embodiments, FIG. 2 is a diagram illustrating the power transmitting device being in the power transmitting state according to example embodiments, and FIG. 3 is a view illustrating an operation of the power transmitting device being in the power transmitting state according to example embodiments.

Figure 4:
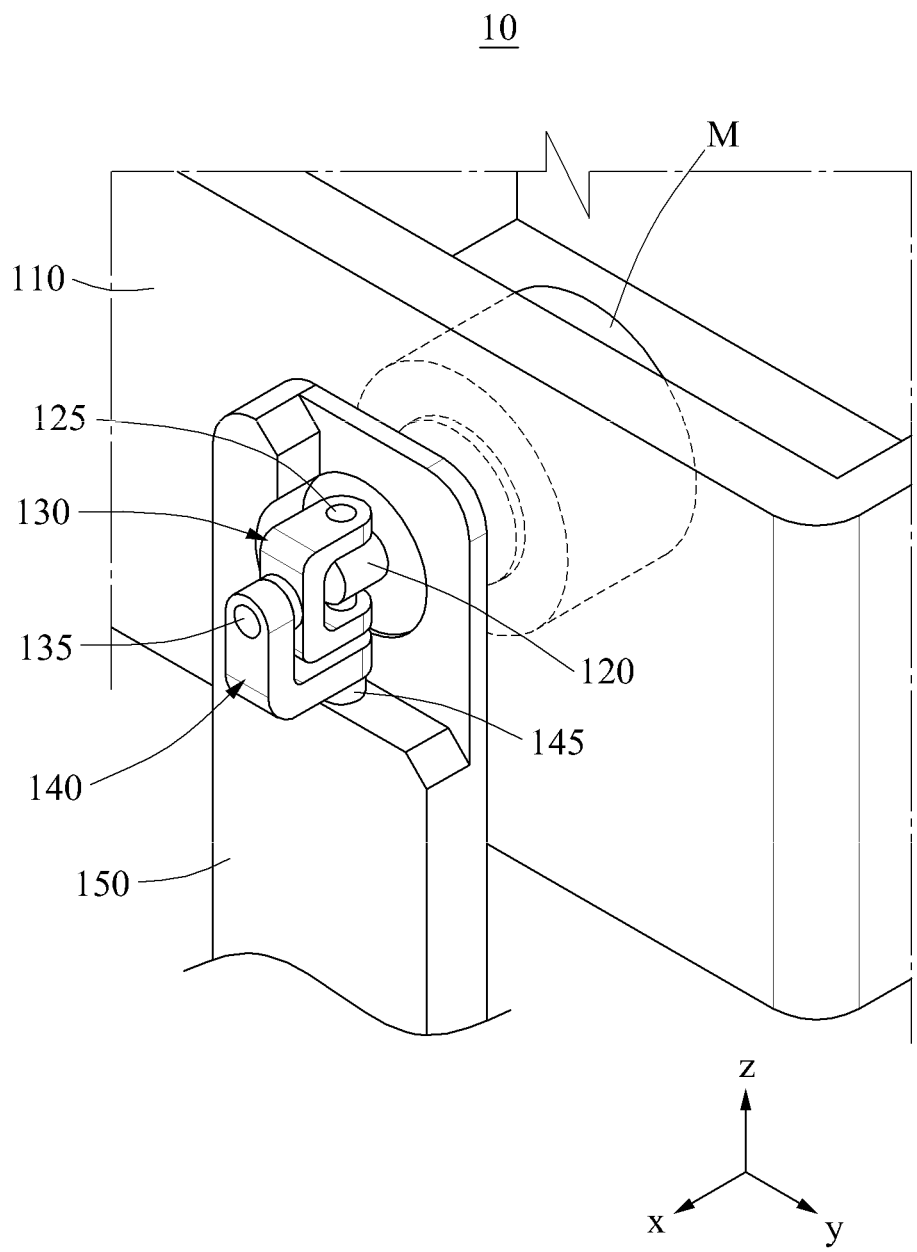
FIG. 4 is a perspective view illustrating a power transmitting device being in a power blocking state according to example embodiments.
Figure 5:
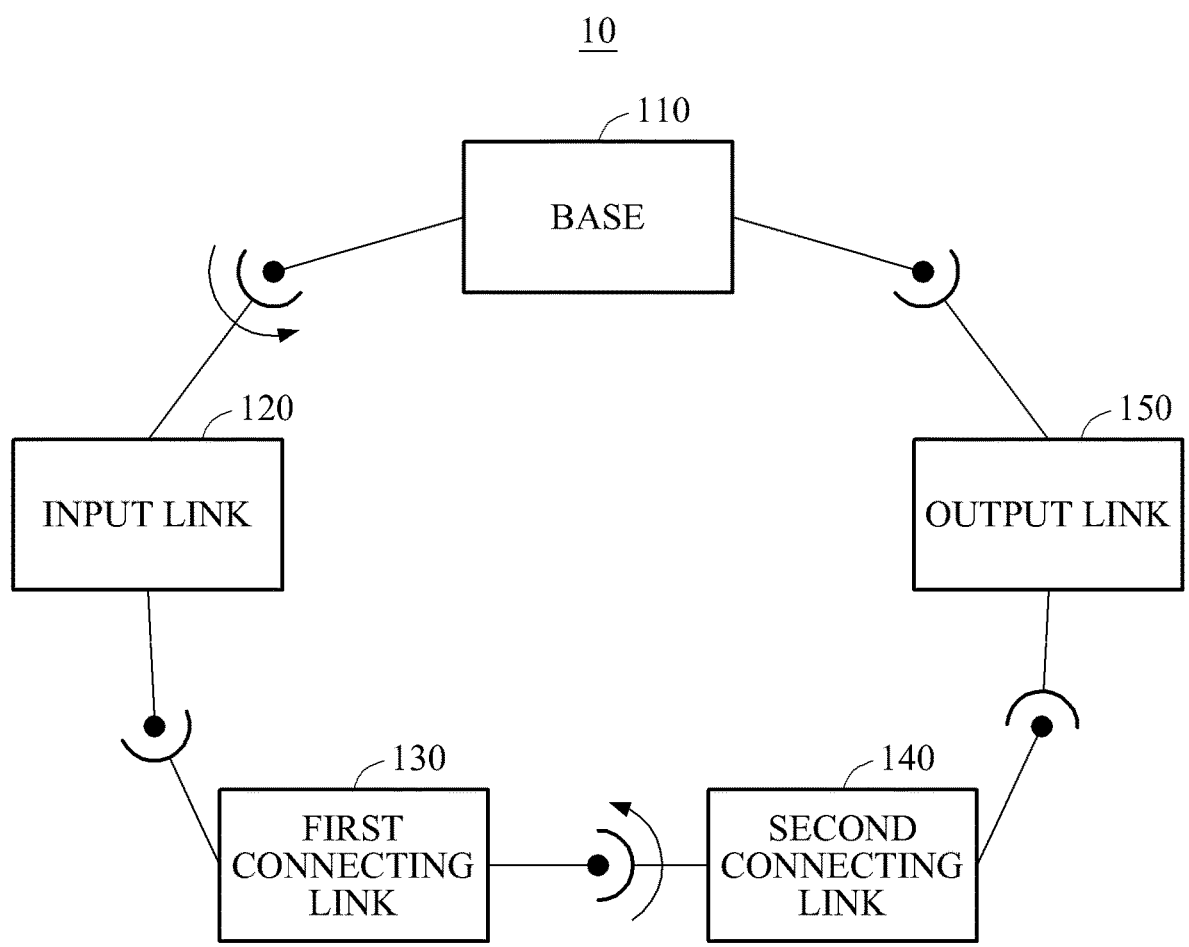
FIG. 5 is a diagram illustrating a power transmitting device being in a power blocking state according to example embodiments.
Figure 6:
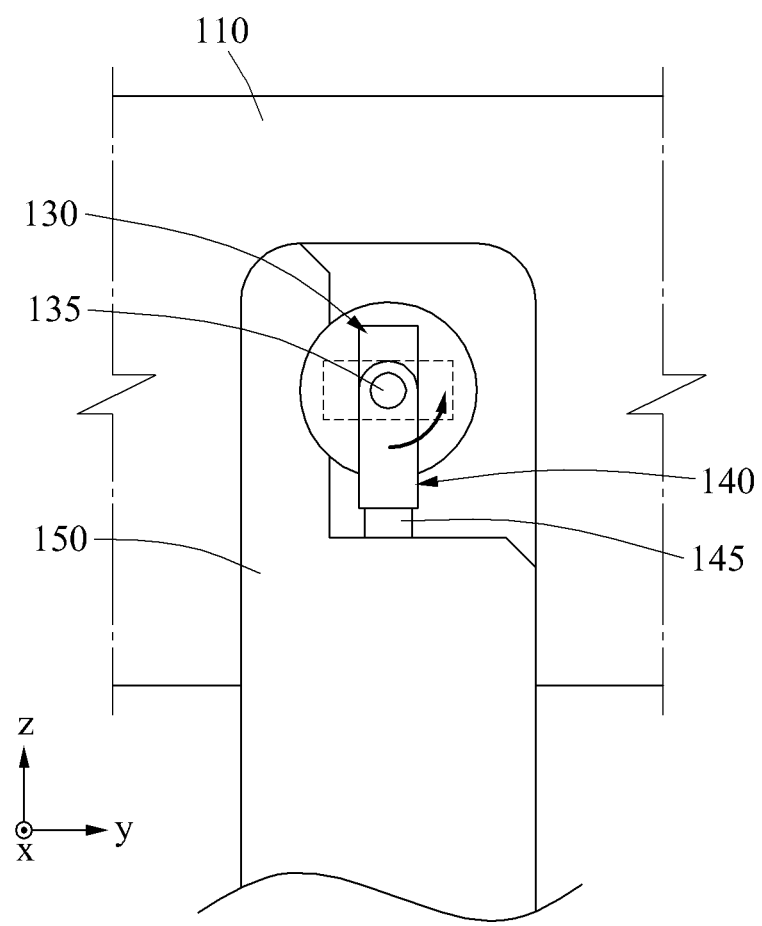
FIG. 6 is a view illustrating an operation of a power transmitting device being in a power blocking state according to example embodiments.

FIG. 4 is a perspective view illustrating the power transmitting device being in a power blocking state according to example embodiments, FIG. 5 is a diagram illustrating the power transmitting device being in the power blocking state according to example embodiments, and FIG. 6 is a view illustrating an operation of the power transmitting device 10 being in the power blocking state according to example embodiments.

Referring to FIGS. 1 through 6, a power transmitting device 10 may include an input link 120, a first shaft 125, a first connecting link 130, a second shaft 135, a second connecting link 140, a third shaft 145, and an output link 150. Based on a power transmission order, the input link 120, the first shaft 125, the first connecting link 130, the second shaft 135, the second connecting link 140, the third shaft 145, and the output link 150 may be sequentially connected to each other.

The input link 120 may rotate with respect to a base 110. For example, the input link 120 may receive power from a driving motor M provided in the base 110.

The first shaft 125 may be connected to the input link 120 in a direction intersecting, for example, orthogonal to, an axial direction of the input link 120. The first shaft 125 may be an independent member capable of rotating with respect to two adjacent links, for example, the input link 120 and the first connecting link 130. As another example, the first shaft 125 may be a member attached to one of the input link 120 and the first connecting link 130 and capable of rotating relative to the other of the input link 120 and the first connecting link 130. Duplicated descriptions with respect to the second shaft 135 and the third shaft 145 will be omitted herein for conciseness.

The first connecting link 130 may be connected to the first shaft 125 and rotate relative to the input link 120.

The second shaft 135 may be connected to the first connecting link 130 in a direction intersecting, for example, orthogonal to, an axial direction of the first shaft 125.

The second connecting link 140 may be connected to the second shaft 135 and rotate relative to the first connecting link 130.

The third shaft 145 may be connected to the second connecting link 140 in a direction intersecting, for example, orthogonal to, an axial direction of the second shaft 135. An axial direction of the third shaft 145 may intersect the axial direction of the input link 120, for example, in an orthogonal direction.

The output link 150 may rotate with respect to the base 110. The output link 150 and the input link 120 may rotate in the same direction. The shaft of the output link 150 may match the shaft of the input link 120. The axial direction of the output link 150 may intersect the axial direction of the third shaft 145, for example, in an orthogonal direction. The axial direction of the output link 150 may intersect the axial direction of the first shaft 125, for example, in an orthogonal direction.

The bent polygonal shapes of the input link 120, the first connecting link 130, the second connecting link 140, and the output link 150 of FIGS. 1 through 6 are examples, and the input link 120, the first connecting link 130, the second connecting link 140, and the output link 150 may be provided in desired (or, alternatively, predetermined) shapes, for example, doughnut shapes, circular shapes, or spherical shapes.

Hereinafter, an operation of the power transmitting device 10 will be described based on, for example, a case in which each pair of adjacent shafts, based on the power transmission order, among the shaft of the input link 120, the first shaft 125, the second shaft 135, the third shaft 145, and the shaft of the output link 150, are orthogonal to each other.

Power input into the input link 120 may be either transmitted to the output link 150 or blocked based on a rotation angle of the second connecting link 140. In detail, based on whether the axial direction of the input link 120 matches the axial direction of the second shaft 135, the power input into the input link 120 may be transmitted to the output link 150 or blocked.

As shown in FIGS. 1 through 3, in a state in which the second connecting link 140 does not rotate, in detail, in a state in which the rotation angle of the second connecting link 140 is 0 degrees based on a z axis, the axial direction of the input link 120 may not match the axial direction of the second shaft 135. In this example, since all of the pairs of adjacent links among the input link 120, the first connecting link 130, the second connecting link 140, and the output link 150 may structurally perform a single rigid body motion, the input link 120 and the output link 150 may perform a single rigid body motion. Thus, based on the power transmission order, all of the input link 120, the first connecting link 130, the second input link 140, and the output link 150 may rotate with respect to the base 110, and the power may be transmitted from the input link 120 to the output link 150. In detail, when the axial direction of the input link 120 does not match the axial direction of the second shaft 135, the power may be transmitted.

As shown in FIGS. 4 through 6, in a state in which the second connecting link 140 rotates, in detail, in a state in which the rotation angle of the second connecting link 140 is 90 degrees based on the z axis, the axial direction of the input link 120 may match the axial direction of the second shaft 135. In this example, the power input into the input link 120 may be transmitted to only components disposed between the input link 120 and the second shaft 135, and may not be transmitted to components connected after the second shaft 135 between the input link 120 and the output link 150. Thus, although power is input into the input link 120, the input power may be used to rotate the input link 120 and the first connecting link 130, and may not rotate the second connecting link 140 and the output link 150. In detail, when the axial direction of the input link 120 matches the axial direction of the second shaft 135, the power may be blocked.

Meanwhile, when all of the input link 120, the first connecting link 130, the second connecting link 140, and the output link 150 rotate as shown in FIGS. 1 through 3, a moment of inertia applied to the driving motor M may be maximized. When only the input link 120 and the first connecting link 130 rotate as shown in FIGS. 4 through 6, the moment of inertia applied to the driving motor M may be minimized.

When the second connecting link 140 is slightly out of the state shown in FIGS. 1 through 3, the shafts of the input link 120, the first connecting link 130, the second connecting link 140, and the output link 150 may be automatically arranged to be in the state in which the moment of inertia decreases, for example, in the state shown in FIGS. 4 through 6. In detail, the state of the power transmitting device 10 shown in FIGS. 1 through 3 may be referred to as being at a singular point. When the second connecting link 140 is at the singular point, the power input into the input link 120 may be transmitted to the output link 150. When the second connecting link 140 is away from the singular point, the power may be blocked.

Although a case in which the power transmitting device 10 includes two connecting links, for example, the first connecting link 130 and the second connecting link 140, and three shafts, for example, the first shaft 125, the second shaft 135, and the third shaft 145, is described, the number of the connecting links and the number of the shafts are not limited thereto. For example, in some example embodiments, the power transmitting device 10 may include any configuration including a plurality of connecting links connected between an input link and an output link and capable of transmitting or blocking power based on a rotation angle of one of the plurality of connecting links. In detail, when one of the plurality of connecting links is at a singular point, power input into the input link may be transmitted to the output link. When one of the plurality of connecting links is away from the singular point, the power may be blocked.

The power transmitting device 10 may switch between transmitting and blocking power through a structural change, rather than completely separating a portion of the plurality of components associated therewith. Dissimilar to a method of selectively transmitting power using a frictional force, for example, a clutch, the power transmitting device 10 may not require a bulky configuration to endure a frictional force, and thus may be miniaturized. Further, the power transmitting device 10 may increase energy efficiency by reducing energy that would be wasted if the power was blocked using a frictional energy. In addition, because the frictional force to block power may not be applied, the durability of the power transmitting device 10 may increase and the lifespan of a product including the power transmitting device 10 may increase. The power transmitting device 10 may be relatively easily manufactured, and have advantages in terms of relatively lower failure and maintenance. Dissimilar to a method of selectively transmitting power by engaging or disengaging gears, the power transmitting device 10 may not require a clearance for separation and coupling. Thus, backlash may not occur due to the reengaging of gears. Since backlash may not need to be considered, the power transmitting device 10 may be easily designed and controlled more accurately. For example, the power transmitting device 10 may be used for a robot arm which requires precise control.

Figure 7:
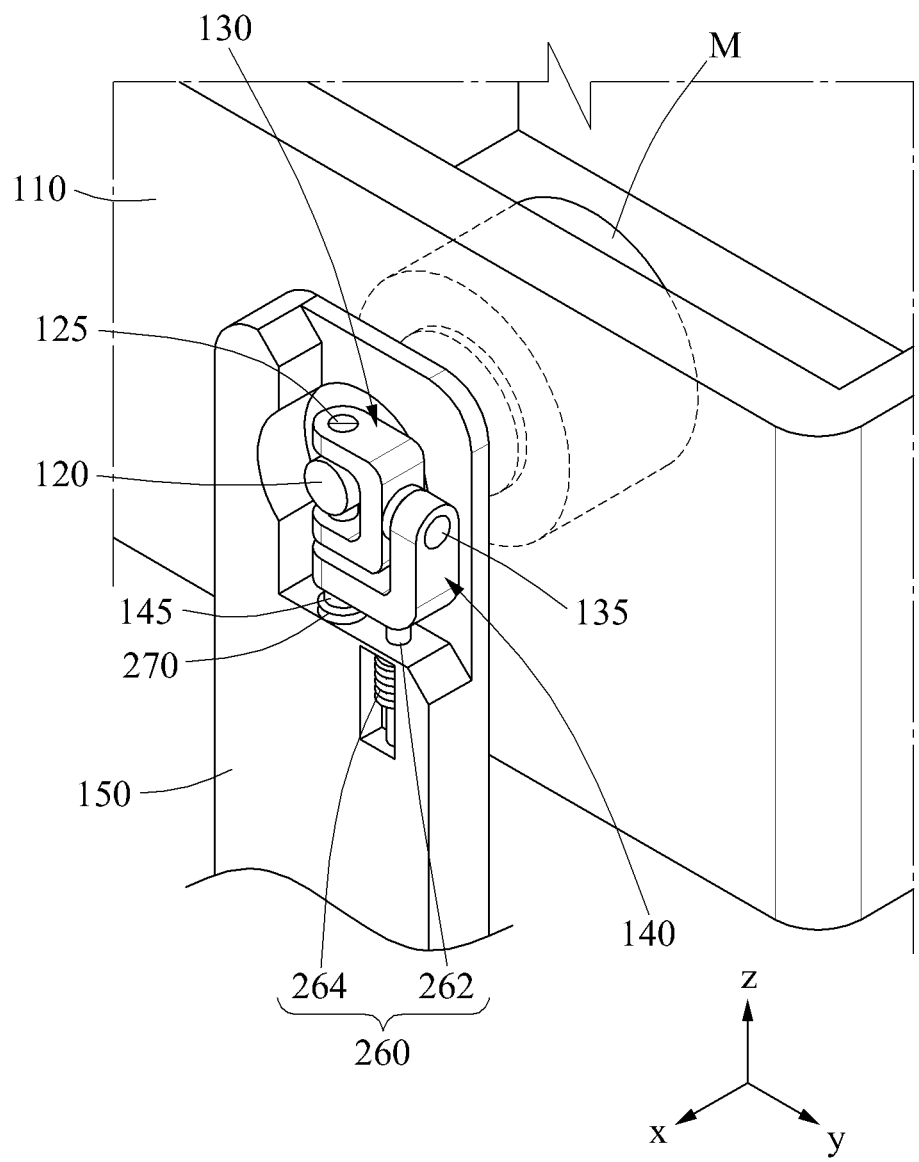
FIG. 7 is a perspective view illustrating a power transmitting device according to example embodiments.

FIG. 7 is a perspective view illustrating a power transmitting device according to other example embodiments.

Referring to FIG. 7, a power transmitting device 20 may include the input link 120, the first shaft 125, the first connecting link 130, the second shaft 135, the second connecting link 140, the third shaft 145, the output link 150, and a locking device 260.

The locking device 260 may maintain an angle of the second connecting link 140. In detail, the locking device 260 may maintain a relative angle formed by the second shaft 135 with respect to the shaft of the input link 120.

For example, the locking device 260 may maintain a state in which power is transmitted from the input link 120 to the output link 150. In detail, the locking device 260 may maintain a state in which the axial direction of the input link 120 does not match the axial direction of the second shaft 135. In further detail, the locking device 260 may restrict the power transmitting device 10 to stay at a singular point.

The locking device 260 may include a stopper 262 and a first elastic member 264.

The stopper 262 may move relative to the output link 150, and restrict a movement of the second connecting link 140. For example, the stopper 262 may be disposed on one side of the output link 150, and move upward in FIG. 7 to be inserted into a recess formed on a bottom of the second connecting link 140, thereby fixing the second connecting link 140.

The first elastic member 264 may provide an elastic force to the stopper 262 such that the stopper 262 may restrict the movement of the second connecting link 140. For example, the first elastic member 264 may be a compression spring configured to pressurize the stopper 262 upward in FIG. 7.

The power transmitting device 20 may further include a second elastic member 270. The second elastic member 270 may provide an elastic force to the second shaft 135 such that the relative angle formed by the second shaft 135 with respect to the shaft of the input link 120 may change when the locking device 260 is released. The second elastic member 270 may provide an elastic force to the second connecting link 140 such that the second connecting link 140 may move to be separated from the stopper 262.

For example, the second elastic member 270 may provide the elastic force to the second connecting link 140 to move the second connecting link 140 such that power may be blocked. In detail, the second elastic member 270 may provide the elastic force to rotate the second connecting link 140 such that the axial direction of the second shaft 135 is the same as the axial direction as the input link 120. The second elastic member 270 may be provided in the third shaft 145. The second elastic member 270 may be a torsion spring configured to provide an elastic force to rotate the second connecting link 140 clockwise based on a z axis such that the second shaft 135 has a same axial direction as the axial direction of the input link 120.

When the locking device 260 is released, the second elastic member 270 may rapidly move the second connecting link 140, thereby relatively rapidly blocking power. Further, to move the second connecting link 140 in a power transmitting direction, the second connecting link 140 is to be moved using a force greater than the elastic force of the second elastic member 270. Thus, unintended power transmission by a mistake of a user or a malfunction of the apparatus may be prevented.

Figure 8:
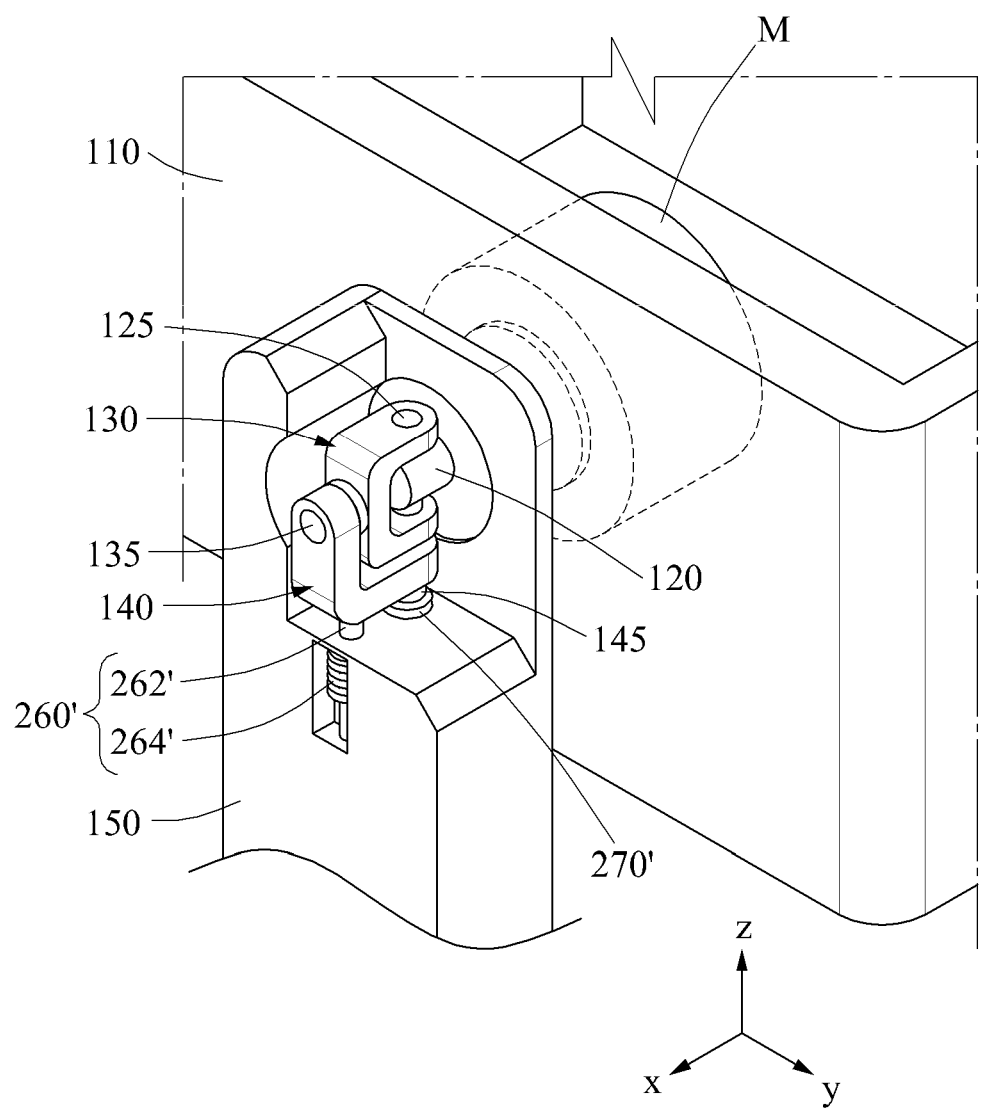
FIG. 8 is a perspective view illustrating a power transmitting device according to example embodiments.

FIG. 8 is a perspective view illustrating a power transmitting device according to other example embodiments.

Referring to FIG. 8, a locking device 260' of a power transmitting device 20' may maintain a state in which power to be transmitted from the input link 120 to the output link 150 is blocked. In detail, contrary to FIG. 7, the locking device 260' may maintain a state in which the axial direction of the input link 120 matches the axial direction of the second shaft 135.

A second elastic member 270' of the power transmitting device 20' may provide an elastic force to the second connecting link 140 such that power may be transmitted. In detail, the second elastic member 270' may be provided in the third shaft 145. The second elastic member 270' may be a torsion spring configured to provide an elastic force to rotate the second connecting link 140 counterclockwise based on a z axis.

Figure 9:
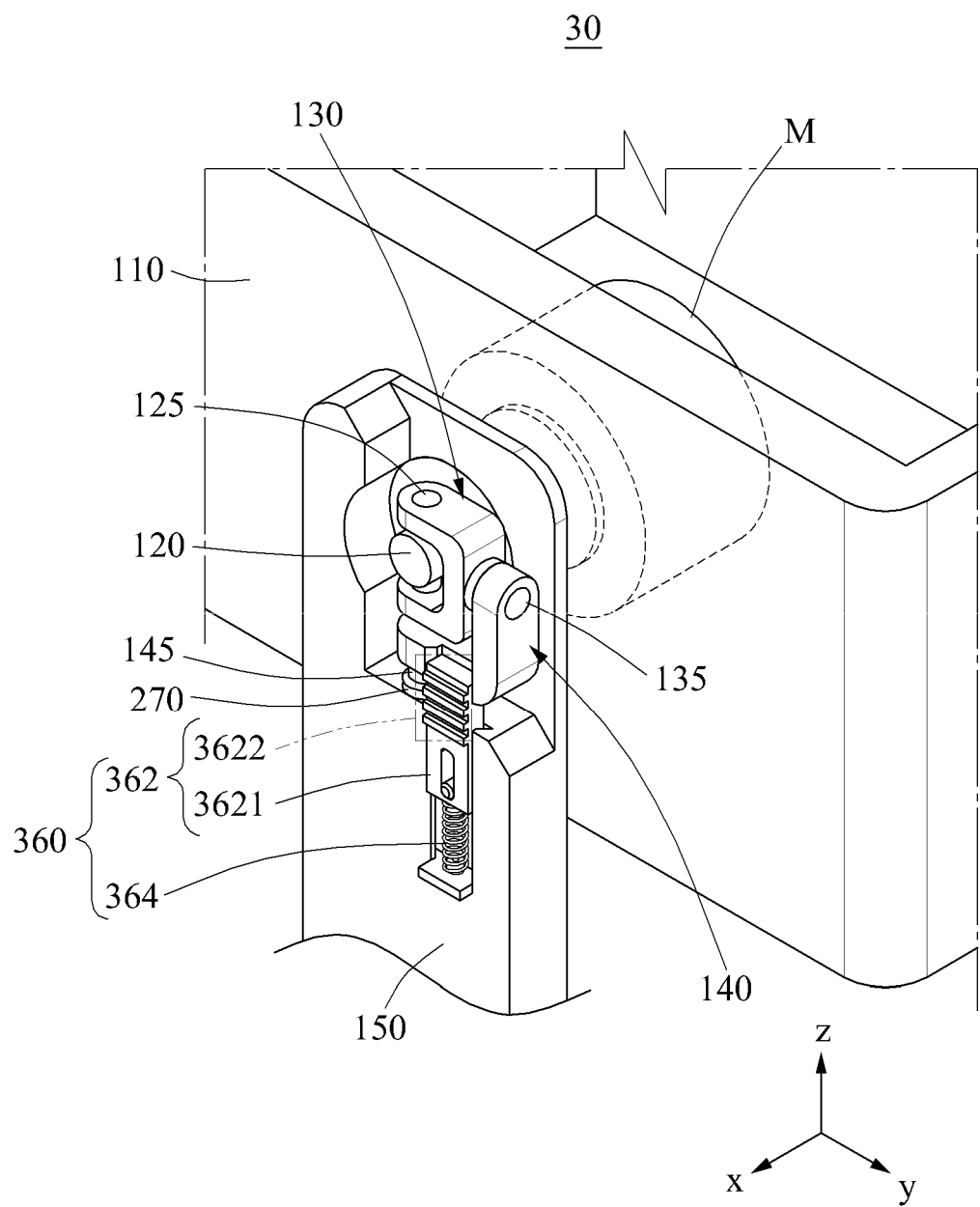
FIG. 9 is a perspective view illustrating a power transmitting device according to example embodiments.

FIG. 9 is a perspective view illustrating a power transmitting device according to other example embodiments.

Referring to FIG. 9, a power transmitting device 30 may include the input link 120, the first shaft 125, the first connecting link 130, the second shaft 135, the second connecting link 140, the third shaft 145, the output link 150, and a locking device 360. The locking device 360 may include a stopper 362 and a first elastic member 364.

The stopper 362 may include a stopper body 3621 connected to the first elastic member 364 and configured to slide with respect to the output link 150, and a grip 3622 connected to the stopper body 3621 and to be gripped by a user. As necessary, the user may move the stopper 362 by controlling the grip 3622 to transmit power from the input link 120 to the output link 150 or block the power. In detail, the user may manually control the stopper 362 to switch the power transmitting device 30 between the power transmitting state and the blocking state.

Figure 10:
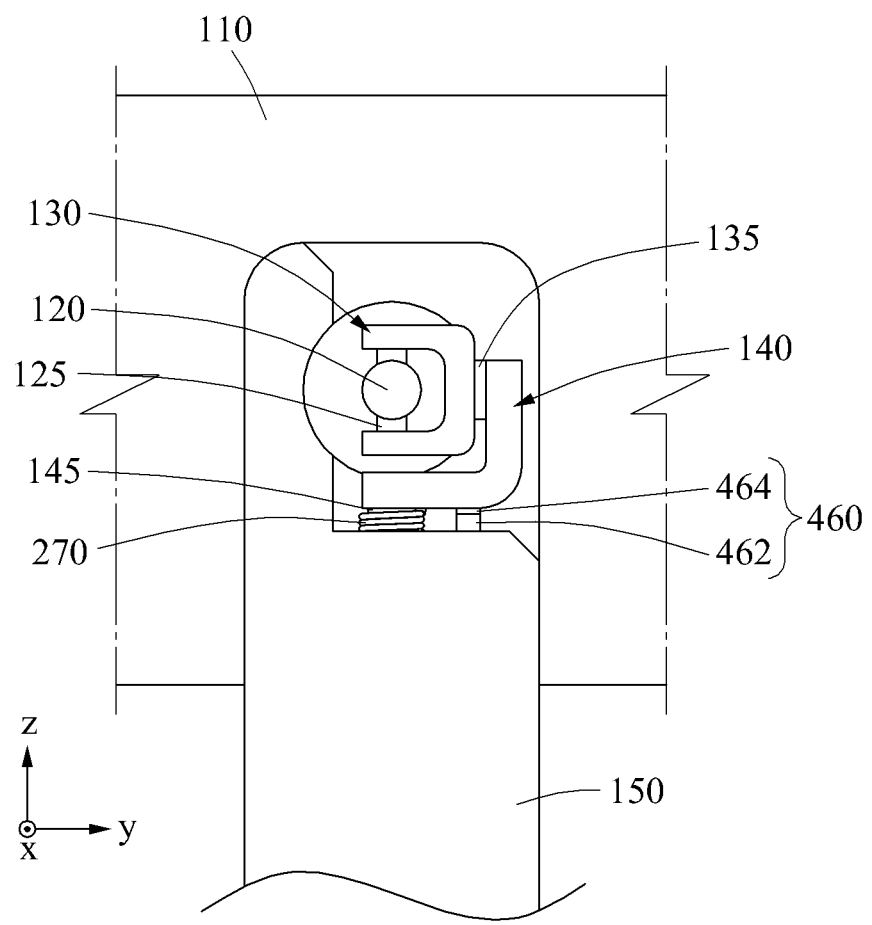
FIG. 10 is a front view illustrating a power transmitting device according to example embodiments.
Figure 11:
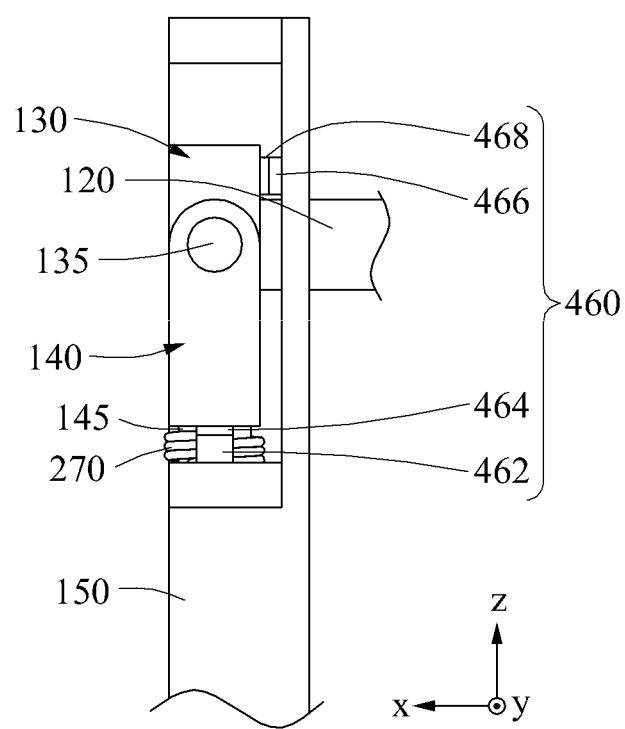
FIG. 11 is a side view illustrating a power transmitting device according to example embodiments.

FIG. 10 is a front view illustrating a power transmitting device according to other example embodiments, and FIG. 11 is a side view illustrating the power transmitting device 40 according to other example embodiments.

Referring to FIGS. 10 and 11, a power transmitting device 40 may include the input link 120, the first shaft 125, the first connecting link 130, the second shaft 135, the second connecting link 140, the third shaft 145, the output link 150, and a locking device 460.

The locking device 460 may fix the first connecting link 130 or the second connecting link 140 using magnetism. The locking device 460 may be provided in the output link 150. The locking device 460 may include at least one magnetic body to be magnetically coupled to at least one of the first connecting link 130 and the second connecting link 140.

For example, the locking device 460 may include a first magnetic body 462 configured to magnetically couple the second connecting link 140 to the output link 150 at a position of a power transmitting state, and a first metal tip 464 provided in the second connecting link 140 at a position corresponding to the position of the first magnetic body 462. The positions of the first magnetic body 462 and the first metal tip 464 may be reversed. When the second connecting link 140 is a conductor, the first metal tip 464 may be omitted. By including the first metal tip 464, a material of the second connecting link 140 may be freely selected such that the second connecting link 140 may be formed of non-magnetic materials.

Similarly, the locking device 460 may include a second magnetic body 466 configured to magnetically couple the first connecting link 130 to the output link 150 in a position of the power transmitting state, and a second metal tip 468 provided in the first connecting link 130 at a position corresponding to the position of the second magnetic body 466.

Figure 12:
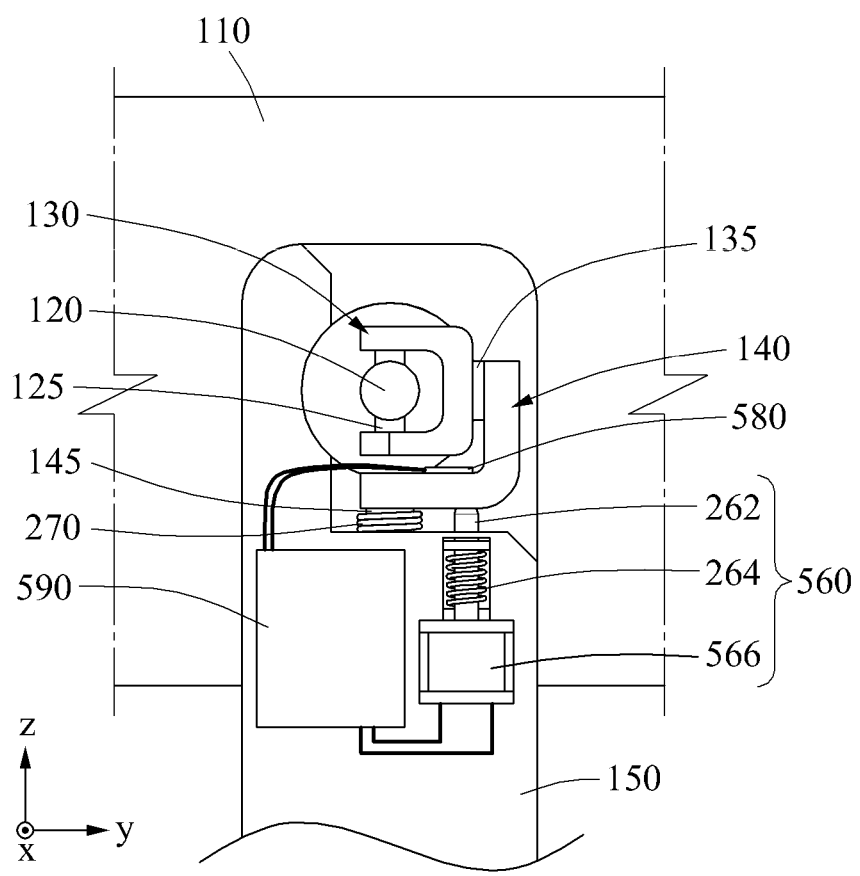
FIG. 12 is a view illustrating a power transmitting device according to example embodiments.

FIG. 12 is a view illustrating a power transmitting device according to other example embodiments.

Referring to FIG. 12, the power transmitting device 50 may include the input link 120, the first shaft 125, the first connecting link 130, the second shaft 135, the second connecting link 140, the third shaft 145, the output link 150, a locking device 560, a sensor 580, and a controller 590.

The locking device 560 may transmit or block power based on whether a current is applied. The locking device 560 may include the stopper 262, the first elastic member 264, and a solenoid 566.

The stopper 262 may restrict a movement of the second connecting link 140. The first elastic member 264 may provide an elastic force in a first direction in which the stopper 262 restricts the movement of the second connecting link 140.

The solenoid 566 may provide an electromagnetic force to the stopper 262 such that the stopper 262 may move in a direction in which the stopper 262 does not restrict the movement of the second connecting link 140, in detail, in a second direction opposite to the first direction, when a current is applied.

The sensor 580 may sense information related to a load applied to at least one of the input link 120, the first shaft 125, the first connecting link 130, the second shaft 135, the second connecting link 140, the third shaft 145, and the output link 150. For example, the sensor 580 may include a strain gauge attached to at least one of the input link 120, the first shaft 125, the first connecting link 130, the second shaft 135, the second connecting link 140, the third shaft 145, and the output link 150. As another example, the sensor 580 may include a pressure sensor attached between two adjoining components to measure a pressure applied between the two components. The type of the sensor 580 is not limited thereto. For example, the sensor 580 may include any device capable of sensing information related to loads applied to the components of the power transmitting device 50.

The controller 590 may control the locking device 560 based on the information sensed by the sensor 580. The controller 590 may release the locking device 560 when a value of the information sensed by the sensor 580 exceeds a set value (or, alternatively, a desired threshold). The controller 590 may prevent an excessive load applied to the components of the power transmitting device 50, whereby damage to the power transmitting device 50 may be prevented and user safety may improve.

Figure 13:
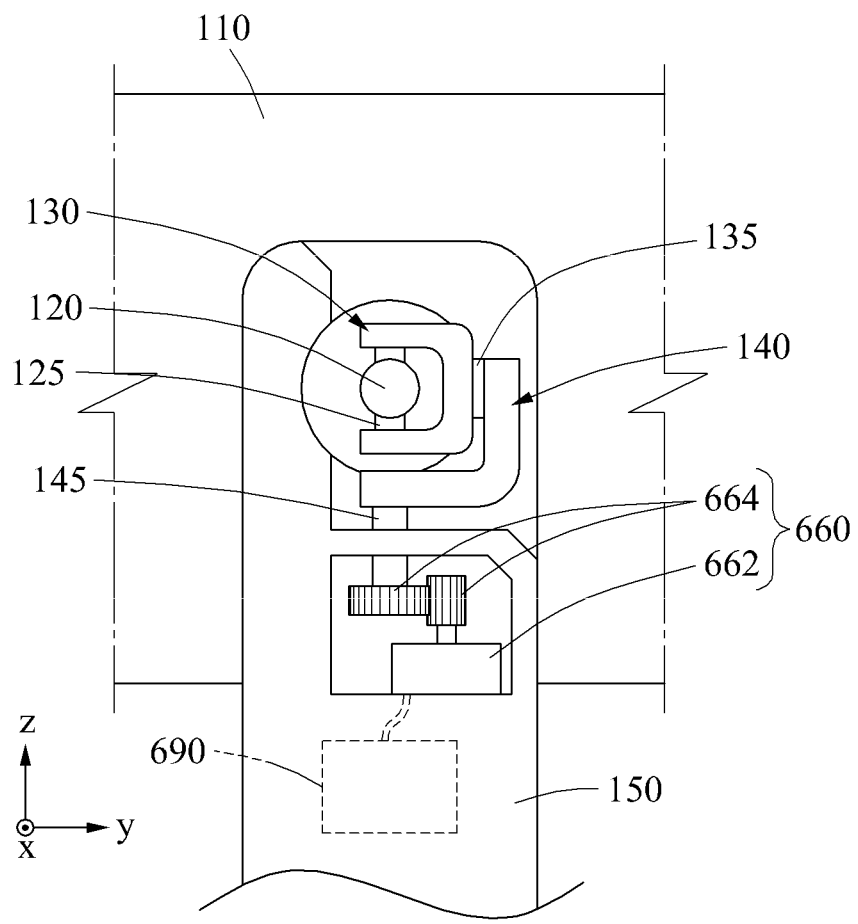
FIG. 13 is a view illustrating a power transmitting device according to example embodiments.

FIG. 13 is a view illustrating a power transmitting device according to other example embodiments.

Referring to FIG. 13, a power transmitting device 60 may include the input link 120, the first shaft 125, the first connecting link 130, the second shaft 135, the second connecting link 140, the third shaft 145, the output link 150, a locking device 660, and a controller 690.

The locking device 660 may include a control motor 662 configured to adjust a rotation angle of the third shaft 145. The control motor 662 may adjust a rotation angle of a motor shaft in response to a signal received from the controller 690. The control motor 662 may include, for example, a servo-motor configured to control a position. The control motor 662 may include, for example, an encoder configured to measure the rotation angle of the motor shaft.

The locking device 660 may further include a decelerator 664 configured to connect the control motor 662 and the third shaft 145 together. By the decelerator 664, the rotation angle of the third shaft 145 may be adjusted more precisely.

The controller 690 may control the control motor 662 to transmit power input into the input link 120 to the output link 150 or block the power. For example, the controller 690 may receive information related to the rotation angle of the third shaft 145 from the encoder provided in the control motor 662, and control the control motor 662 based on the received information.

Figure 14:
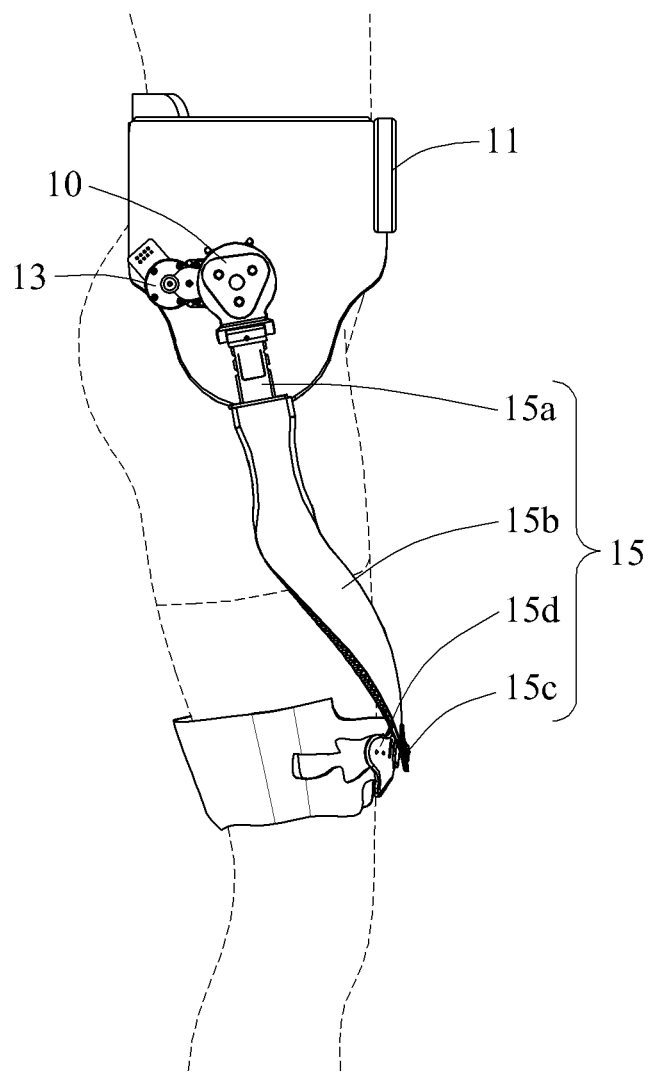
FIG. 14 is a view illustrating a motion assistance apparatus according to example embodiments.

FIG. 14 is a view illustrating a motion assistance apparatus according to example embodiments.

Referring to FIG. 14, a motion assistance apparatus 1 may be worn by a user to assist a motion of the user.

The user may correspond to a human, an animal, or a robot. However, the user is not limited thereto. In addition, although FIG. 14 illustrates a case in which the motion assistance apparatus 1 assists motions of thighs of the user, the motion assistance apparatus 1 may also assist a motion of an upper body, for example, a hand, an upper arm, and a lower arm of the user. Further, the motion assistance apparatus 1 may assist a motion of another part of a lower body, for example, a foot, and a calf of the user. The motion assistance apparatus 1 may assist a motion of a part of the user. Hereinafter, a case in which the motion assistance apparatus 1 assists motions of thighs of a human will be described. However, example embodiments are not limited thereto.

The motion assistance apparatus 1 may include a fixing module 11, (or alternatively, referred to as a fixing device), a driving module 13, (or, alternatively, referred to as a driver), the power transmitting device 10, and a supporting module 15 (or, alternatively, referred to as a support).

In some example embodiments, the driving module 13, the power transmitting device 10 and the supporting module 15 may be provided in plural and a first one of the driving module 13, the power transmitting device 10 and the supporting module 15 may be associated with one leg of the user, and a second one of the driving module 13, the power transmitting device 10 and the supporting module 15 may be associated with another leg of the user.

The fixing module 11 may be attached to the user. The fixing module 11 may cover an outer surface of the user. For example, the fixing module 11 may be attached to the sides of a waist of the user, and include a curved surface corresponding to a contact portion of the user.

The driving module 13 may provide power to be transmitted to the power transmitting device 10. For example, the driving module 13 may be disposed in a lateral direction of the power transmitting device 10 such that a rotation axis of the driving module 13 may be spaced apart from a rotation axis of the power transmitting device 10. In this example, when compared to a case in which the driving module 13 and the power transmitting device 10 share a rotation axis, a protruding height from the user may relatively decrease. In other example embodiments, the driving module 13 may be more spaced apart from the power transmitting device 10. In this example, a power transmitting module may be additionally provided to transmit power from the driving module 13 to the power transmitting device 10. The power transmitting module may be a rotary body such as, for example, a gear, or a longitudinal member such as, for example, a wire, a cable, a string, a rubber band, a spring, a belt, and a chain.

The power transmitting device 10 may receive power from the driving module 13, and transmit the power to the supporting module 15 to assist a motion of a joint portion of the user. The power transmitting device 10 may be disposed on one side of the fixing module 11 at a position corresponding to the joint portion of the user. An input end of the power transmitting device 10 may be connected to the driving module 13, and an output end of the power transmitting device 10 may be connected to the supporting module 15.

The power transmitting device 10 may include an input link configured to rotate with respect to the fixing module 11 and receive power from the driving module 13, an output link configured to rotate with respect to the fixing module 11 and transmit the power to the supporting module 15, and a plurality of connecting links connected between the input link and the output link. The power generated by the driving module 13 may be transmitted to the output link or blocked based on a rotation angle of one of the plurality of connecting links.

In this example, by transmitting or blocking the power based on a walking state of the user, the user safety may improve. Further, the power may be transmitted at a singular point, and thus a response rate may improve in that the power may be blocked rapidly. In addition, when the power is blocked, the output link may freely rotate without being affected by moments of inertia of the input link and a rotor of the driving module 13 connected to the input link. Thus, when a battery is completely discharged, the user may move without experiencing a great resistance although the user is still wearing the motion assistance apparatus 1, whereby the usability of the motion assistance apparatus 1 may increase. Further, when testing an effect of the motion assistance apparatus 1 on the user, an effect of the weight of the motion assistance apparatus 1 may be tested while excluding an effect of an assistance force, and thus the product test may be easily performed.

The supporting module 15 may support another portion of the user, for example, a thigh of the user, and assist a motion of a lower limb of the user. The supporting module 15 may include a connecting member 15a, a power transmitting frame 15b, an applying member 15c, and a supporting member 15d.

The connecting member 15a may be hinge-connected to, for example, the power transmitting device 10. A hinge axis of the connecting member 15a may be disposed in a direction intersecting, for example, orthogonal to, a shaft of the output link of the power transmitting device 10. In this example, the supporting module 15 may perform a two degree of freedom (DOF) motion with respect to the fixing module 11.

The power transmitting frame 15b may transmit force to a portion of the user. One end portion of the power transmitting frame 15b may be rotatably connected to the connecting member 15a, and another end portion of the power transmitting frame 15b may be connected to the applying member 15c to transmit force to a portion of the user. For example, the power transmitting frame 15b may push or pull a thigh of the user. The power transmitting frame 15b may extend and be bent in a longitudinal direction of the thigh of the user to cover a portion of a circumference of the thigh of the user. The one end portion of the power transmitting frame 15b may be disposed on a side surface of the thigh of the user, and the other portion of the power transmitting frame 15b may be disposed on a front surface of the thigh of the user. A surface on the side of the one end portion of the power transmitting frame 15b may be orthogonal to a surface on the side of the other end portion of the power transmitting frame 15b.

The power transmitting frame 15b may be movably connected to the connecting member 15a. By relative motions of the power transmitting frame 15b and the connecting member 15a, a total length from the power transmitting device 10 to the applying member 15c may be variable. In this example, the supporting module 15 may perform a three DOF motion with respect to the fixing module 11.

The applying member 15c may be connected to the other end portion of the power transmitting frame 15b to apply force to a portion of the user. For example, the applying member 15c may be disposed along the front surface of the thigh of the user, or in a circumferential direction of the thigh of the user to push or pull the thigh of the user. The applying member 15c may include a curved surface corresponding to the thigh of the user, and configured to extend from the other end portion of the power transmitting frame 15b toward both sides of the power transmitting frame 15b.

The supporting member 15d may be connected to one side of the applying member 15c. For example, the supporting member 15d may be disposed to cover a circumference of at least a portion of the thigh of the user, thereby preventing separation of the thigh of the user from the power transmitting frame 15b.

In some example embodiments, an additional driving module and/or supporting module may be provided. For example, the supporting module 15 may extend to a knee, and an additional joint device may be provided in the supporting module 15 at a position corresponding to a knee joint. Further, an additional supporting module may be connected to the additional joint device. The additional supporting module may support a calf of the user, thereby assisting a motion of the calf. Here, an actuator configured to drive the additional joint device may be disposed on one side of the additional joint device, or may be disposed in, for example, the fixing module 11, to be spaced apart from the additional joint device.

Figure 15:
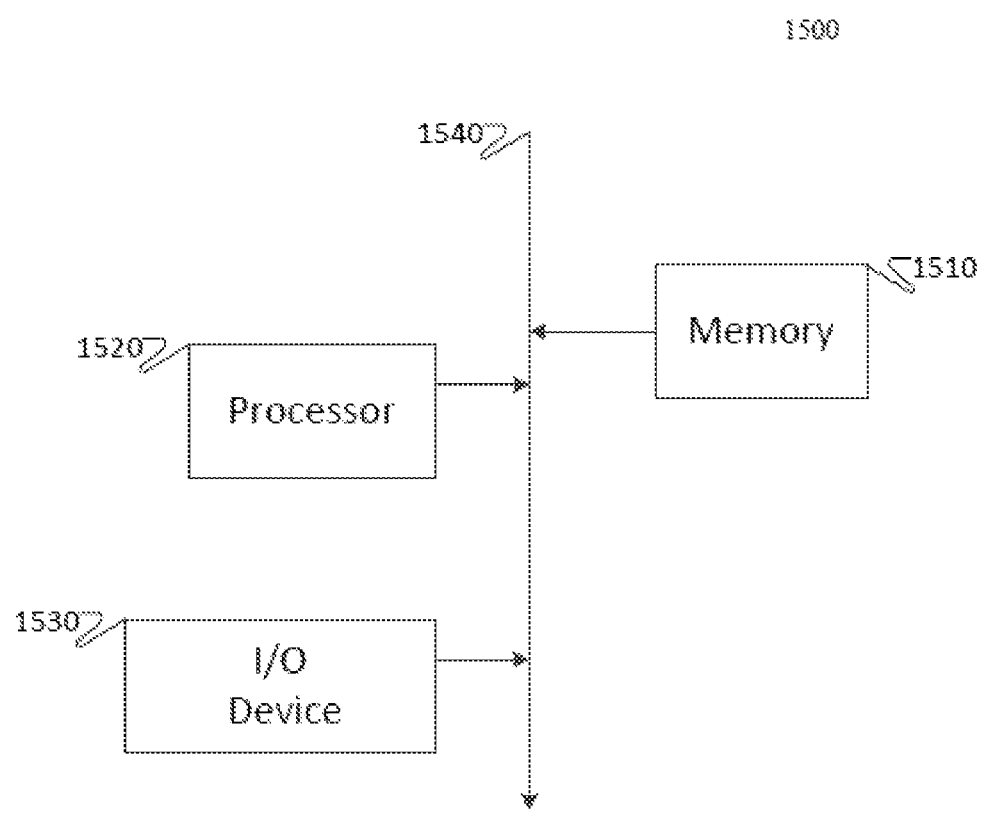
FIG. 15 illustrates a controller of a motion assistance apparatus according to example embodiments.

FIG. 15 illustrates a controller of a motion assistance apparatus according to example embodiments.

Referring to FIG. 15, a controller 1500 may include a memory 1510, a processor 1520, an input/output (I/O) device 1530, and a bus 1540 connecting same. The controller 1500 may be mounted on, for example, the fixing module 11. The controller 1500 may be an example of one or more of the controller 590 illustrated in FIG. 12 or the controller 690 illustrated in FIG. 13.

The I/O device 1530 may include transmitters and/or receivers. The transmitters may include hardware and any necessary software for transmitting signals including, for example, data signals and/or control signals to the driver 13 and/or the power transmission device 10. The receivers may include hardware and any necessary software for receiving signals including, for example, data signals and/or control signals from one or more sensors, for example, the sensor 580.

The memory 1510 may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The processor 1520 may be implemented by at least one semiconductor chip disposed on a printed circuit board. The processor 1520 may be an arithmetic logic unit, a digital signal processor, a microcomputer, a field programmable array, a programmable logic unit, a microprocessor or any other device capable of responding to and executing instructions in a defined manner.

The processor 1520 may be programmed with instructions that configure the processor 1520 into a special purpose computer to perform the operations illustrated in one or more of FIGS. 16, 17A and 17B, discussed below. For example, the processor 1620 may transmit, via the I/O device 1530, control instructions to control the driver 13 and/or power transmission device 10 based on information provided by the sensors. For example, the processor 1520 may transmit control instructions to the power transmission device 10 to selectively unlock a lock associated with the power transmission device based on a force sensed by one or more of the sensors, for example, the sensor 580.

Further, in some example embodiments, the processor 1520 may receive, via the I/O device 1530, signals from one or more sensors including information associated with a movement of the wearer. For example, the sensors may be pressure sensors located on a sole of the wearer, potentiometer that senses joint angles or joint angular velocities, or an inertial measurement unit (IMU) sensor that measures acceleration information while the user is ambulatory. The processor 1520 may determine that the wearer is walking with difficulty, for example, that the wearer is moving slower than a normal pace associated with the wearer, based on the information from the sensors, and transmit a control instruction to the power transmission device 10 to selectively transmit the power from the driving module 13 to the support 15 if the user is experiencing difficulty walking.

Figure 16:
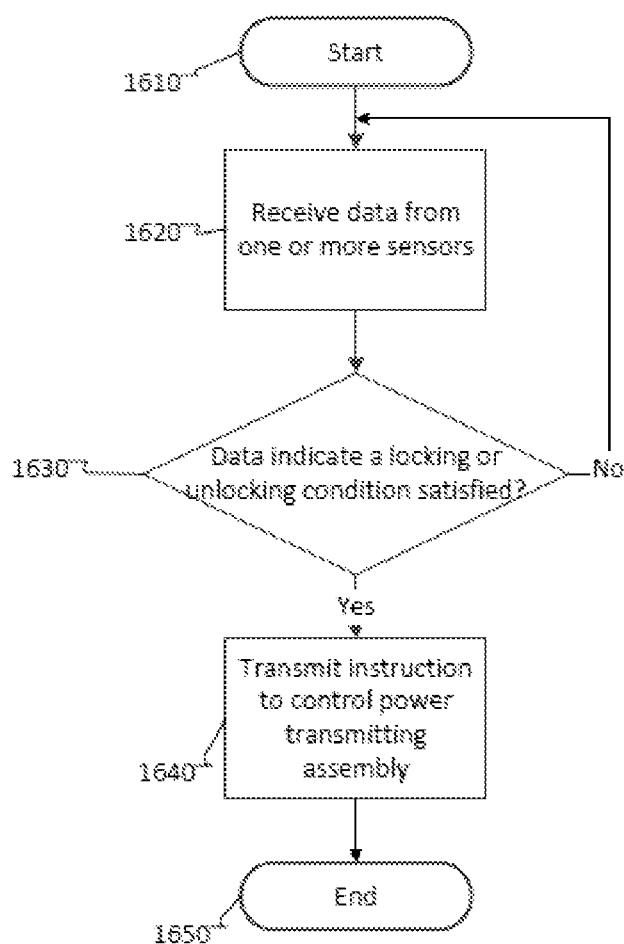
FIG. 16 illustrates a method of controlling a motion assistance apparatus according to example embodiments.

FIG. 16 illustrates a method of controlling a motion assistance apparatus according to example embodiments.

Referring to FIG. 16, in operation 1610 the controller 1500 may initialize.

In operation 1620, the controller 1500 may receive data from one or more sensors. For example, the controller 1500 may receive, via the I/O device 1530, data from the sensor 580 and/or pressure sensors located on a sole of the user.

In operation 1630, the controller 1500 may determine whether the data indicates a locking/unlocking condition is satisfied.

In operation 1640, the controller 1500 may transmit an instruction to control the power transmitting device based on a whether the locking/unlocking condition is satisfied. For example, the controller 1500 may transmit, via the I/O deice 1530, an instruction to set the power transmitting device 10 to one of the power transmitting state and the power blocking state based on whether the locking or unlocking condition is satisfied.

Figure 17A:
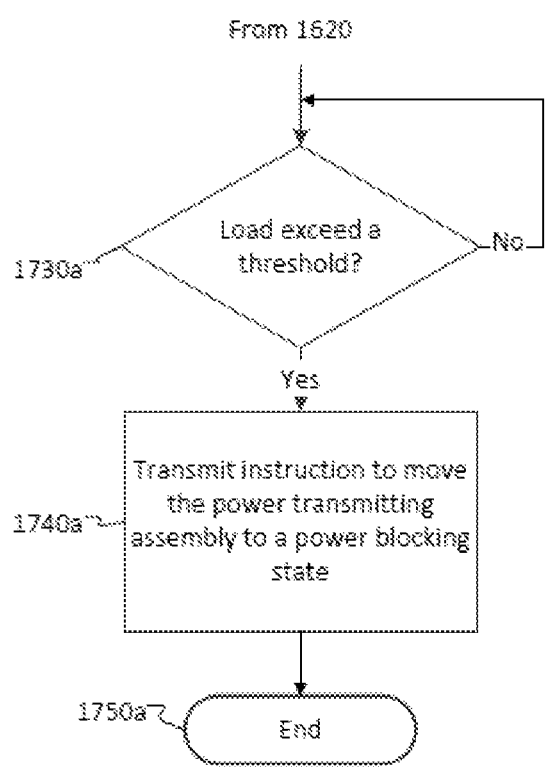
FIGS. 17A and 17B illustrates methods of controlling a motion assistance apparatus according to example embodiments.
Figure 17B:
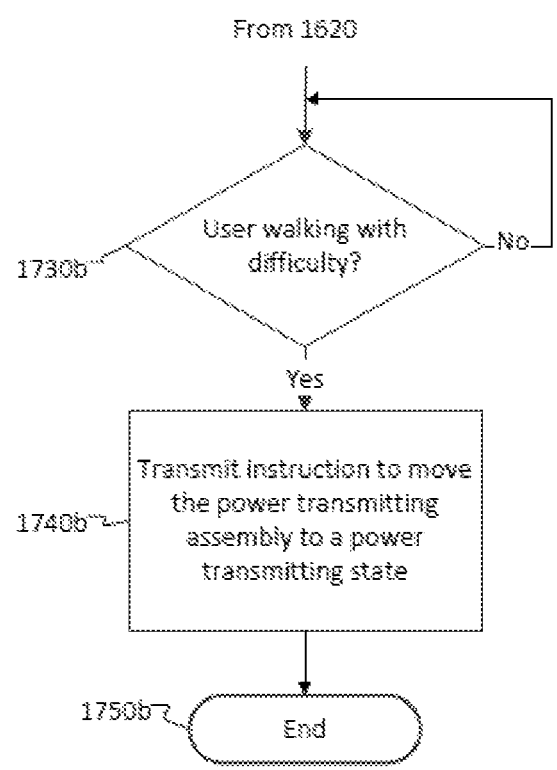

FIGS. 17A and 17B illustrate methods of controlling a motion assistance apparatus according to example embodiments.

Referring to FIGS. 16 to 17B, in some example embodiments, in operation 1730a, the controller 1500 may determine a load applied to components of the power transmitting device 10 exceeds a threshold based on the data received from the sensors in operation 1620. In operation 1740a, the controller 1500 may transmit an instruction to move the power transmitting device 10 to a power blocking state, if the controller 1500 determines that the load exceeds the threshold. Therefore, the controller 1500 may protect the motion assistance apparatus 1 by preventing an excessive load applied thereto.

In other example embodiments, in operation 1730b, the controller 1500 may determine whether the user is walking with difficulty based on the data received from the sensors in operation 1620. In operation 1740b, the controller 1500 may transmit an instruction to move the power transmitting device 10 to a power transmitting state, if the controller 1500 determines that the user is walking with difficulty. Therefore, the controller 1500 may allow the motion assistance apparatus 1 to automatically assist the user with motion.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A motion assistance apparatus comprising:
 a fixing device configured to attach to a first portion of a user;
 a support configured to support a second portion of the user;
 a driver configured to generate power; and
 a power transmitting device configured selectively transmit the power between the driver and the support, the power transmitting device including,
  an input link configured to rotate with respect to a base;
  an output link configured to rotate with respect to the base;
  a first shaft connected to the input link in a direction intersecting an axial direction of the input link;
  a first connecting link connected to the first shaft;
  a second shaft connected to the first connecting link in a direction intersecting an axial direction of the first shaft;
  a second connecting link connected to the second shaft; and
  a third shaft connected between the second connecting link and the output link in a direction intersecting an axial direction of the second shaft.

2. The motion assistance apparatus of claim 1, wherein the output link and the input link are configured to rotate in a same direction.

3. The motion assistance apparatus of claim 1, wherein the second shaft is configured to one of transfer power and block power between into the input link and the output link based on whether the axial direction of the input link matches the axial direction of the second shaft.

4. The motion assistance apparatus of claim 1, wherein
 the axial direction of the first shaft is orthogonal to the axial direction of the input link,
 the axial direction of the second shaft is orthogonal to the axial direction of the first shaft,
 an axial direction of the third shaft is orthogonal to the axial direction of the second shaft, and
 an axial direction of the output link is orthogonal to the axial direction of the third shaft.

5. The motion assistance apparatus of claim 1, wherein an axial direction of the third shaft is orthogonal to the axial direction of the input link.

6. The motion assistance apparatus of claim 1, wherein an axial direction of the output link is orthogonal to the axial direction of the first shaft.

7. The motion assistance apparatus of claim 1, further comprising:
a locking device configured to maintain a relative angle formed by the second shaft with respect to a shaft of the input link.

8. The motion assistance apparatus of claim 7, wherein the locking device comprises:
a stopper configured to move relative to the output link to restrict a movement of the second connecting link.

9. The motion assistance apparatus of claim 8, wherein the locking device further comprises:
a first elastic member configured to provide an elastic force to the stopper in a direction that restricts the movement of the second connecting link.

10. The motion assistance apparatus of claim 9, further comprising:
a second elastic member configured to provide an elastic force to the second connecting link to urge the second connecting link to separate from the stopper.

11. The motion assistance apparatus of claim 9, wherein the stopper comprises:
a stopper body associated with the first elastic member, the stopper body configured to slide with respect to the output link; and
a grip associated with the stopper body, the grip configured to provide friction to a user when the user grips the grip.

12. The motion assistance apparatus of claim 7, wherein the locking device comprises:
a magnetic body configured to magnetically couple the output link to least one of the first connecting link and the second connecting link.

13. The motion assistance apparatus of claim 7, further comprising:
a sensor configured to sense information related to a load applied to at least one of the input link, the output link, the first shaft, the first connecting link, the second shaft, the second connecting link, and the third shaft; and
a controller configured to control the locking device based on the information sensed by the sensor.

14. The motion assistance apparatus of claim 13, wherein the controller is configured to release the locking device when a value of the information sensed by the sensor exceeds a threshold.

15. The motion assistance apparatus of claim 14, wherein the locking device comprises:
a stopper configured to restrict a movement of the second connecting link;
a first elastic member configured to provide an elastic force to the stopper in a first direction such that the stopper restricts the movement of the second connecting link; and
a solenoid configured to provide an electromagnetic force to the stopper to move the stopper in a second direction opposite to the first direction when a current is applied such that the movement of the second connecting link is unrestricted by the stopper.

16. The motion assistance apparatus of claim 7, further comprising:
a second elastic member configured to provide an elastic force to the second shaft such that the relative angle between the second shaft and the shaft of the input link changes when the locking device is released.

17. The motion assistance apparatus of claim 16, wherein the second elastic member is configured to provide the elastic force to the second connecting link such that power transfer between the input link and the output link is blocked.

18. The motion assistance apparatus of claim 16, wherein the second elastic member is configured to provide the elastic force to the second shaft such that the second shaft rotates in a same direction as the axial direction of the input link.

19. The motion assistance apparatus of claim 7, wherein the locking device comprises:
a control motor configured to adjust a rotation angle of the third shaft.

20. The motion assistance apparatus of claim 1, wherein the first connecting link is connected to the second connecting link, and the first connecting link is configured to pivot between a first position in which the first connecting link transmits the power generated by the input link to the second connecting link and a second position in which the first connecting link not transmit the power to the second connecting link.

21. The motion assistance apparatus of claim 20, wherein, in the second position, the first connecting link is configured spin about the second shaft such that the power is not transmitted to the second rotatable link.

22. The motion assistance apparatus of claim 20, wherein, in the second position, the input link and the second shaft are aligned.

23. The motion assistance apparatus of claim 22, wherein, in the second position, the input link and the second shaft are aligned such that the axial direction of the input link is same as the axial direction of the second shaft.

24. The motion assistance apparatus of claim 22, wherein, in the second position, the first connecting link and the second connecting link remain connected.

25. The motion assistance apparatus of claim 20, further comprising:
a releasable lock configured to selectively lock the first connecting link at a first one of the first position and the second position.

26. The motion assistance apparatus of claim 25, further comprising:
a spring configured to rotate the first connecting link to a second one of the first position and the second position, if the releasable lock is unlocked.

27. A motion assistance apparatus comprising:
a fixing device configured to attach to a first portion of a user;
a support configured to support a second portion of the user;
a driver configured to generate power; and
a power transmitting device configured selectively transmit the power between the driver and the support, the power transmitting device including,
an input link including a drive shaft configured to receive the power from the driver;
an output link connected to the support; and
a plurality of connecting links connected between the drive shaft and the output link, the plurality of connecting links configured to transmit or block transmission of the power to the output link based on a rotation angle of at least one of the plurality of connecting links configured to rotate about a first shaft connected to the drive shaft and extending in a direction intersecting the drive shaft.

28. The motion assistance apparatus of claim 27, wherein an axial direction of the drive shaft and an axial direction of a shaft of the output link are collinear.

29. The motion assistance apparatus of claim 27, wherein the plurality of connecting links comprise:
- a first connecting link configured to rotate relative to the input link; and
- a second connecting link configured to rotate relative to the first connecting link.

30. The motion assistance apparatus of claim 29, wherein the second connecting link is the one of the plurality of connecting links such that the plurality of connecting links transmit or block the power to the output link based on the rotation angle of the second connecting link.

31. The motion assistance apparatus of claim 27, wherein the plurality of connecting links transmit the power to the output link when the rotation angle places the one of the plurality of connecting links at a set position.

32. The motion assistance apparatus of claim 27, further comprising:
- a sensor configured to sense information associated with a movement of the user; and
- a controller configured,
  - determine whether the user is experiencing difficulty moving based on the information, and
  - transmit an instruction to the power transmitting device to transmit the power, if the user is experiencing difficulty moving.

* * * * *